US010603003B2

(12) United States Patent
Bailey et al.

(10) Patent No.: US 10,603,003 B2
(45) Date of Patent: Mar. 31, 2020

(54) CT SYSTEMS FOR IMAGING OF THE BREAST

(71) Applicant: Dedicated2Imaging, LLC, Portsmouth, NH (US)

(72) Inventors: Eric M. Bailey, North Hampton, NH (US); Andrew Tybinkowski, Silver Lake, NH (US)

(73) Assignee: Dedicating2Imaging, LLC, Portsmouth, NH (US)

(*) Notice: Subject to any disclaimer, the term of this patent is extended or adjusted under 35 U.S.C. 154(b) by 0 days.

(21) Appl. No.: 16/074,102

(22) PCT Filed: Apr. 11, 2017

(86) PCT No.: PCT/US2017/026923
§ 371 (c)(1),
(2) Date: Jul. 31, 2018

(87) PCT Pub. No.: WO2017/180570
PCT Pub. Date: Oct. 19, 2017

(65) Prior Publication Data
US 2019/0357868 A1 Nov. 28, 2019

Related U.S. Application Data

(60) Provisional application No. 62/322,256, filed on Apr. 14, 2016.

(51) Int. Cl.
A61B 6/02 (2006.01)
A61B 6/00 (2006.01)
(Continued)

(52) U.S. Cl.
CPC .............. *A61B 6/502* (2013.01); *A61B 6/027* (2013.01); *A61B 6/035* (2013.01); *A61B 6/0435* (2013.01);
(Continued)

(58) Field of Classification Search
None
See application file for complete search history.

(56) References Cited

U.S. PATENT DOCUMENTS 6,987,831 B2 * 1/2006 Ning ..................... A61B 6/032
378/20
7,609,808 B2 10/2009 Tornai et al.
(Continued)

OTHER PUBLICATIONS

Shah, Jainil P., et al. "Design of a nested SPECT-CT system with fully suspended CT sub-system for dedicated breast imaging." Medical Imaging 2014: Physics of Medical Imaging. vol. 9033. International Society for Optics and Photonics, 2014.
(Continued)

*Primary Examiner* — Thomas R Artman

(57) ABSTRACT

In example embodiments, a CT imaging system is provided comprising opposing x-ray generation and x-ray detector assemblies and a motion mechanism configured for simultaneously rotationally orbiting the x-ray generation and x-ray detector assemblies around a patient's anatomy along a main axis of rotation of the imaging system while rotationally oscillating the x-ray generation and x-ray detector assemblies about a spinning oscillation axis which is perpendicular to both the main axis of rotation and to a transmission axis extending between the x ray generation and detector assemblies. Further improvements related to a patient support platform and a biopsy attachment are also described herein.

20 Claims, 3 Drawing Sheets

(51) Int. Cl.
*A61B 6/03* (2006.01)
*A61B 6/04* (2006.01)
(52) U.S. Cl.
CPC .......... *A61B 6/4085* (2013.01); *A61B 6/4233* (2013.01); *A61B 6/4423* (2013.01)

(56) References Cited

U.S. PATENT DOCUMENTS

| | | | |
|---|---|---|---|
| 7,697,660 B2 * | 4/2010 | Ning | A61B 6/032 378/37 |
| 2004/0081273 A1 * | 4/2004 | Ning | A61B 6/032 378/37 |
| 2006/0094950 A1 * | 5/2006 | Ning | A61B 6/032 600/407 |
| 2007/0036418 A1 | 2/2007 | Pan et al. | |
| 2009/0171244 A1 * | 7/2009 | Ning | A61B 6/032 600/567 |
| 2011/0033024 A1 | 2/2011 | Dafni et al. | |
| 2015/0173690 A1 * | 6/2015 | Ning | A61B 6/032 600/427 |
| 2017/0258413 A1 * | 9/2017 | Ning | A61B 6/032 |

OTHER PUBLICATIONS

Shah, Jainil P., et al. "Implementation and first results of the fully suspended cone beam CT and SPECT system for dedicated breast imaging." Nuclear Science Symposium and Medical Imaging Conference (NSS/MIC), 2015 IEEE. IEEE, 2015.

* cited by examiner

BREST CT WITH IMAGE-GUIDED BIOPSY PROCEDURES

CT SYSTEMS FOR IMAGING OF THE BREAST

CROSS-REFERENCE TO RELATED SECTIONS

The subject application claims the benefit of U.S. Provisional Application Ser. No. 62/322,256 filed Apr. 14, 2016 and entitled "CT Systems for Imaging of the Breast," the contents of which are hereby incorporated herein in their entirety.

BACKGROUND

The subject application relates to computerized tomography (CT) imaging. In particular, new and improved CT imaging systems are presented which improve the ability to use CT imaging on the breast, e.g., for diagnostic, biopsy, and cancer screening applications.

Example improvements disclosed herein include. The improved CT systems presented herein have many uses across a number of different settings.

Breast cancer is the most common diagnosed cancer among women worldwide. 1 in 8 women will acquire breast cancer in their lifetime. While the death rate has been declining since the 1990's due to screening, early detection, and early treatment, the death rate is still high. 40,000 women died last year in the USA due to breast cancer.

However, breast cancer screening still is still lacking in quality and efficacy. In particular, current cancer screening techniques result in a great number of false positives, and false negatives (in fact, a recent study showed that $4.8B was wasted last year in the USA on false positives and the cost of life is much greater on the false negative front).

One of the main reasons for these deficiencies is that conventional breast cancer screening technologies still utilize 2D imaging. Thus, traditional mammography requires that the breast (a 3D object) be painfully compressed using what essentially amounts to a vice to render it more two dimensional so as to conform to 2D x-ray imaging standards. Beyond obvious discomfort (which can lead, inter alia, to reduced patient compliance) such compression can often result in reduced image reliability, quality and coverage. These deficiencies are particularly evident for women with smaller/denser breasts which can be extremely difficult to image using conventional mammography techniques. Ironically, woman with smaller/denser breasts are already at greater risk with a much higher incidence of cancer.

Thus, there are significant advantages to developing technologies which would enable 3D type scanning of the preset. Unfortunately, traditional 3D scanning machines like MM and CT have lacked the high spatial resolution to see the smallest malignancies.

Devising an effective and accurate breast CT system is not as simple as it sounds. There are several major problems, which a designer must deal with. First is that ordinarily cone beam CT, whereby a transmission trajectory is made around an object in one plane, is plagued by the fact that all tissue does not get irradiated the same, nor spatial sampled/reconstructed the same. This means that lesions in different parts of the field of view will be imaged with much different accuracy. A second problem is in physically rotating in a coronal plane around one breast, but yet getting deep enough to image the breast to the chest wall. This compounded by the fact that patients come in many different sizes. It is not good enough to scan the majority of the breast while omitting the chest wall as many suspicious and malignant lesions are found there. It is not good enough to only be able to scan 50% of the population. An effective product should be able to scan up to 95% or greater of the population.

The subject application relates to U.S. Pat. No. 7,609,808 to Martin P. Tornai et al., entitled "Application specific emission and transmission tomography" and issued Oct. 27, 2009, the entire contents of which are incorporated herein by reference. In particular Tornai teaches a compact and mobile gantry for 3-dimensional imaging of the breast. In Tornai, the imaging device is mounted to a support so as to be selectively movable during imaging in three dimensions, including radial movement relative to a rotation axis, rotational movement about the rotation axis, vertical movement parallel to the rotation axis, and pivoting movement about a pivot axis perpendicular to said rotation axis.

While the imaging device disclosed in Tornai represents some advancement in the optimization and specialization of a 3D type imaging system for the breast, in many ways it is limited by its overly complex and unrefined design intended more as a proof of concept than a viable commercial product. Thus there remains a need for a 3D type imaging system for the breast that can improve upon the initial Tornai design. These and other needs are addressed by way of the present disclosure.

SUMMARY

In example embodiments, a CT imaging system is provided comprising opposing x-ray generation and x-ray detector assemblies and a motion mechanism configured for simultaneously rotationally orbiting the x-ray generation and x-ray detector assemblies around a patient's anatomy along a main axis of rotation of the imaging system while rotationally oscillating the x-ray generation and x-ray detector assemblies about a spinning oscillation axis which is perpendicular to both the main axis of rotation and to a transmission axis extending between the x-ray generation and detector assemblies. While in some embodiments the orbiting and the oscillating motion are independent, in preferred embodiments, the oscillating motion are dependent. Thus, in example embodiments, an orbital position may be determinative of a corresponding oscillation position. Furthermore, the motion mechanism may be configured to result in fixed number of oscillations per orbital rotation (e.g., two or more oscillations per rotation). One possible mechanism for combining the orbital and oscillation motions is using a rotating angled slip ring and bearings. The angles surface of the slip ring can be used to drive the oscillations of the gantry holding the x-ray generation and detector assemblies. In other embodiments, a rotational slip ring can be combined with an oscillating actuator to generate the desired motion. In some embodiments, the x-ray detector assembly may include a high resolution flat-panel x-ray detector.

In example embodiments, the main axis of rotation may be configured to correspond with a longitudinal axis of a cavity configured for receiving a portion of a patient's anatomy to be imaged. In some embodiments, a patient support structure, e.g., made of a radiolucent material, may define the cavity. Advantageously, the patient support structure may include graduated or angled support walls leading to the cavity. For example, the graduated or angled support walls may define a conical or funnel type configuration. In some embodiments, an angle of the support walls may be configured to correspond with a position or orientation of the x-ray generation assembly or the x-ray detection assembly during peak oscillation. In further embodiments, the support walls may also define undulations corresponding with the oscillating motion of the x-ray generation assembly and the x-ray detection assembly. Thus, the undulations may advantageously drive the oscillating motion of the x-ray generation assembly and the x-ray detection assembly. In some embodiments, the cavity may be configured to function as a sealed volumetric cavity once a patient's anatomy is received therein. In example embodiments, the cavity may further include a changeable lining for enabling quick cleaning and sterilization of the cavity. In other embodiments, the patient support structure may include a semi-flexible or elastic support sheath or netting over an opening to the cavity (e.g., configured to stretch and mold to a shape of the patient's anatomy while still providing for support). In yet further embodiments, the patient support structure may include an interchangeable negative mold corresponding to a shape of the patient's anatomy fitted into the cavity and enabling the patient's anatomy to be held in a volumetrically secured position. In some embodiments, the patient support structure may include motorized means for positioning the patient into the supine position.

In example embodiments, the system may also include an integrated biopsy feature including a biopsy attachment. Advantageously, a gantry holding the x-ray generation and x-ray detection assemblies may therefore be configured to enable moving the x-ray generation and x-ray detection assemblies one or more of laterally, vertically or pivotally so as to allow for access for the biopsy attachment from multiple and opposite directions.

BRIEF DESCRIPTION OF THE DRAWINGS

The present disclosure is further described in the detailed description which follows, in reference to the noted plurality of drawings by way of non-limiting examples of embodiments of the present disclosure.

DETAILED DESCRIPTION

Figure 1:
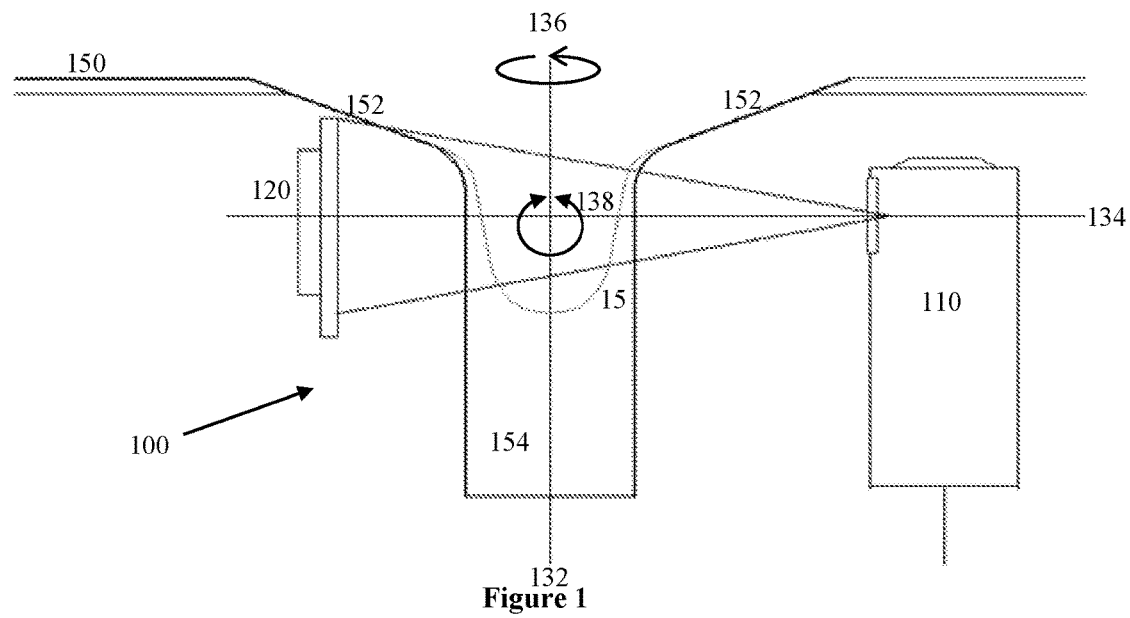
FIG. 1 depicts an example CT imaging system combining orbital and oscillating motion, according to embodiments of the present disclosure.

As noted above, the systems presented herein seek to improve upon the Tornai design and to provide a viable commercial solution for 3D imaging of the breast. Similar to in Tornai, the systems disclosed herein utilize a cone beam breast CT imaging device intended to image a patient's breast while the patient is in a supine position on a support structure. In particular a patient's breast is inserted downward into a cavity formed into the support structure. The breast is thus, suspended along a dorsal-ventral axis of the patient which forms a main axis of rotation for imaging system.

In the imaging device in Tornai, an overly complex set of mechanisms is generally utilized to control the desired motion of the imaging device. For example, in several embodiment, the imaging device in Tornai includes (i) a rotating base platform for controlling rotational movement of the imaging device around a rotational axis (ii) a first translational mechanism for controlling vertical translational moment of the base parallel to the rotational axis (iii) a second translational mechanism for controlling radial translation of the imaging device relative to the base in a radial direction relative to the rotational axis, (iv) a third translational mechanism for controlling lateral translation of the imaging device relative to the base and (v) a pivoting mechanism for pivoting the imaging device relative to the base about a pivot axis. It is also noted that the proposed imaging device in Tornai is general single photon imaging emission system with a single imaging assembly that does not adequately accommodate imaging devices using opposing x-ray generation and x-ray detection assemblies. While a few embodiments in Tornai relate to imaging systems with dual opposing assemblies (see, FIGS. 10A-13B) the proposed 3D movements of such disclosed imaging systems and corresponding control mechanisms are even more complex than other embodiments.

In contrast with the imaging device in Tornai, the subject application proposes a much simplified set of mechanism for controlling desired motion of a CT imaging system including opposing x-ray generation and x-ray detector assemblies (advantageously, the x-ray detector may include a standard high resolution flat-panel x-ray detector such as used in conventional x-ray or fluoroscopic applications). In particular, the proposed CT imaging system includes a simplified motion wherein (i) the opposing x-ray generation and x-ray detector assemblies rotate (orbit) around a main axis of rotation of the imaging system while (ii) the x-ray generation and detector assemblies simultaneously rotationally oscillate about a spinning oscillation axis which is perpendicular to both the main axis of rotation and to a transmission axis between the x-ray generation and detector assemblies. In essence the motion effected is like that of a see-saw mounted on a merry-go-round, wherein opposing ends of the see-saw represent the x-ray generation and detector assemblies. Notably, the rotating and oscillating motions can be independent (e.g., wherein rotational and oscillation positions are independently determined/controlled), or advantageously, in some embodiments, dependent (e.g., wherein rotational positional also determines/controls oscillation position). In some embodiments, the imaging system may be configured to affect a fixed number of oscillations per rotation. For example, in some embodiments, the imaging system may be configured to affect two or more oscillations per rotation. It is notable that many mechanisms may be utilized to affect the desired motion. For example, in some embodiments a bearing may be combined with a specially configured slip ring to create the combined rotational and oscillating motion. In other embodiments, a rotating slip ring may be used in conjunction with an oscillating actuator to produce the desired motion.

Figure 2:
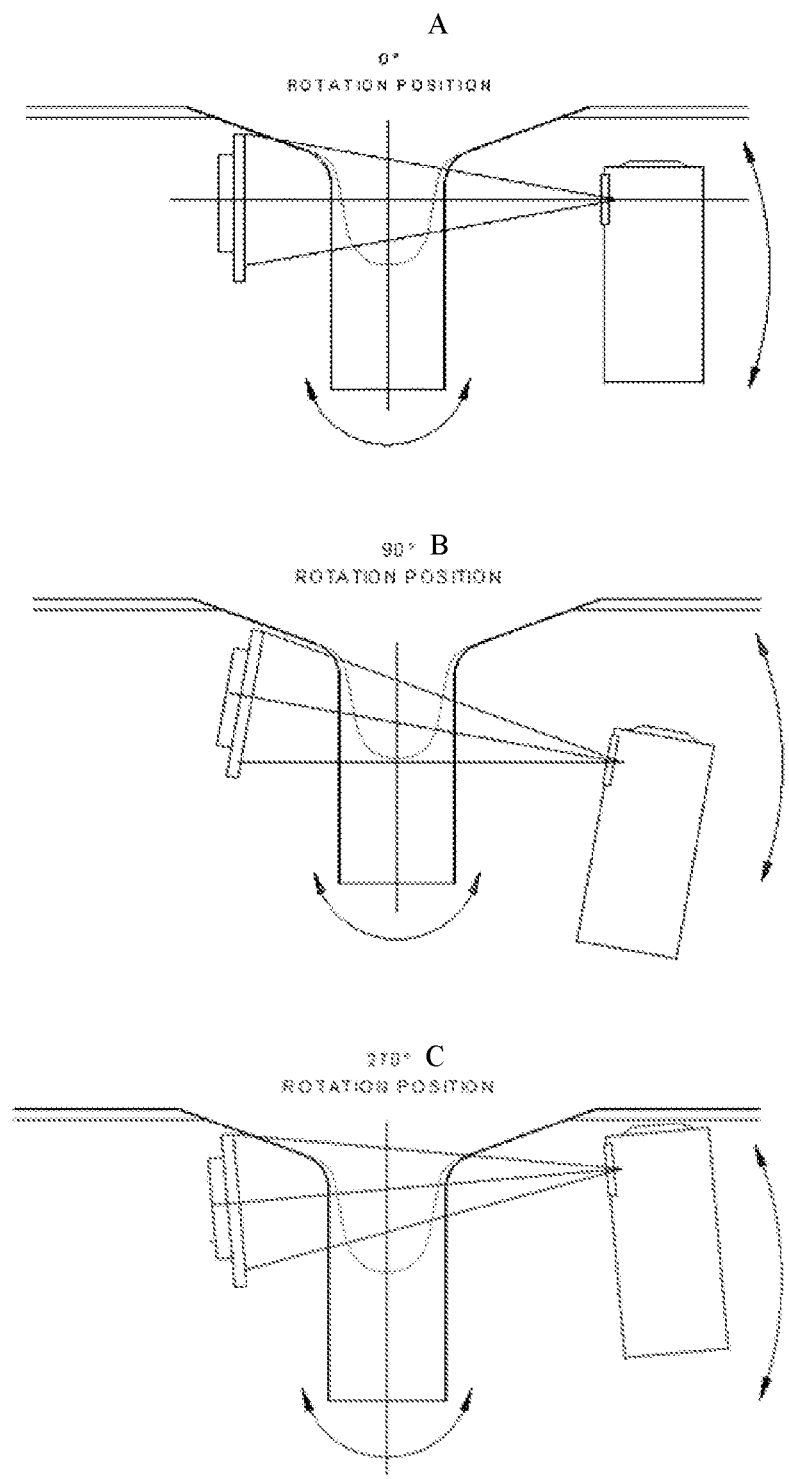
FIGS. 2A-2C illustrate the oscillating motion of the system in FIG. 1, according to embodiments of the present disclosure.
Figure 4:
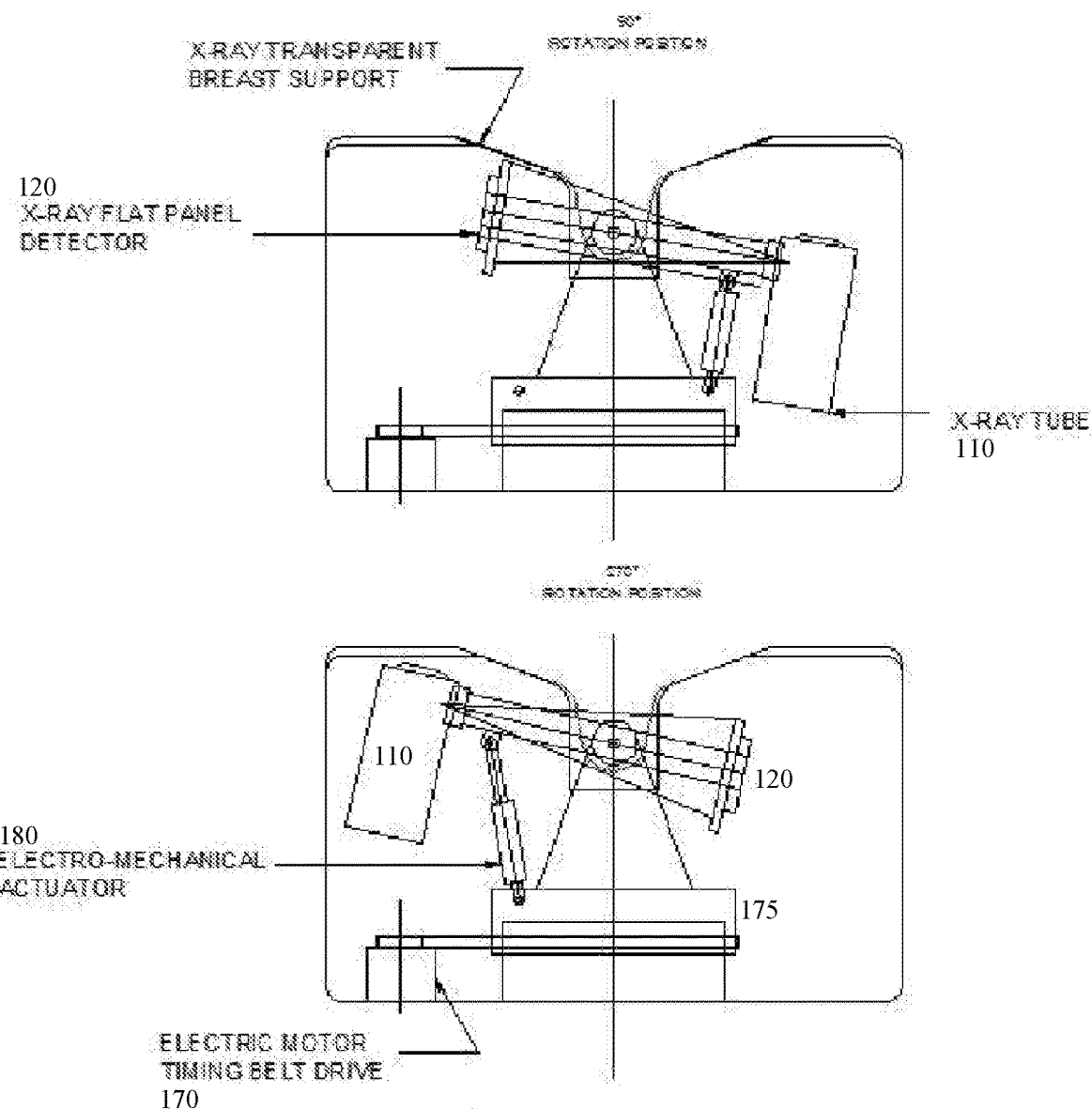
FIG. 4 depicts an example mechanism for producing the orbital and oscillating motions for the imaging system in FIG. 1, according to embodiments of the present disclosure.

FIGS. 1 and 2 illustrate the proposed simplified motion of the imaging systems presented herein. With specific reference to FIG. 1, an example imaging system 100 is depicted including opposing x-ray generation 110 and x-ray detector 120 assemblies. In operation, the imaging system 100 includes a simplified motion wherein (i) the opposing x-ray generation 110 and x-ray detector 120 assemblies rotate (orbit) around a main axis of rotation 132 of the imaging system (which is also a longitudinal axis of a cavity 154 for receiving a portion of a patient's anatomy 15, e.g., a patient's breast) while (ii) the x-ray generation 110 and detector 120 assemblies simultaneously rotationally oscillate 138 about a spinning oscillation axis which is perpendicular to both the main axis of rotation 132 and to a transmission axis 134 between the x-ray generation 110 and detector 120 assemblies (i.e., perpendicular to the plan view of FIG. 1). FIGS. 2A-2C illustrated this oscillation motion, e.g., as the x-ray generation 110 and detector 120 assemblies are rotated between 0, 90 and 270 degree positions respectively.

Advantageously, improved CT imaging systems described herein also improve upon patient support structures for aligning and receiving a patient's anatomy. For example, as illustrated in FIG. 1, in example embodiments, the improved CT imaging system 100 may include a patient support structure 150 which includes graduated or angled support walls 152 leading to the cavity 154 (e.g., a conical or funnel type design). Advantageously these support walls 152 may be constructed from radiolucent material. Moreover, the cavity 154 may be configured to function as a sealed volumetric cavity which is made from x-ray translucent material once a patient's anatomy is received therein. Notably, this cavity may further be configured for easy cleaning/sterilized (e.g., by changing out a disposable inner lining). In some embodiments the support walls 152 may correspond/correlate with a position/orientation of the x-ray generation assembly and/or the x-ray detection assembly during peak oscillation. For example, the support walls 152 may be angled similar to an orientation angle the x-ray generation assembly 110 and/or the x-ray detection assembly 120 during peak oscillation (see, e.g., FIG. 2B). In yet further embodiments the support walls 152 may include built in undulations corresponding with the desired oscillations. Thus, in some embodiments a topography of the support walls 152 may define the oscillation path of the x-ray generation assembly 110 and/or the x-ray detection assembly 120. Thus, the support walls may advantageously drive the oscillations of the imaging system 100 as the s-ray generation assembly 110 and the x-ray detection assembly 120 are rotated around the primary rotational axis 132.

In some embodiments, the patient support structure 150 may further include a semi-flexible or elastic support sheath or netting over the cavity 154 opening which may add to the comfort of the patient by providing support for the breast when inserted into the cavity 154. Advantageously the semi-flexible or elastic support sheath may be configured to stretch/mold to the shape of the patient's anatomy 15 (e.g., breast) while still providing for support. Like the support walls, the support sheath may advantageously be constructed from a substantially radiolucent material. In further example embodiments, the system may be configured to provide (e.g., 3D print) a negative mold shaped like the anatomical feature which is to be imaged. This negative mold may be constructed of a radiolucent material and may in use be fitted into the cavity 154 thereby enabling the patient's anatomy 15 to be held in a volumetrically secured position. Other mechanisms of holding such as clamping or suction force may also be utilized.

In further example embodiments, the patient support structure 150 may also include a motorized means for positioning the patient into the supine position. Thus, e.g., the patient support structure 150 may be configured to pivot (and possibly translate) to move the patient into the supine position and then return the patient to an inclined or vertical position. In other embodiments, the patient support structure 150 may include a mechanism for raising/lowering the patient as well.

Figure 3:
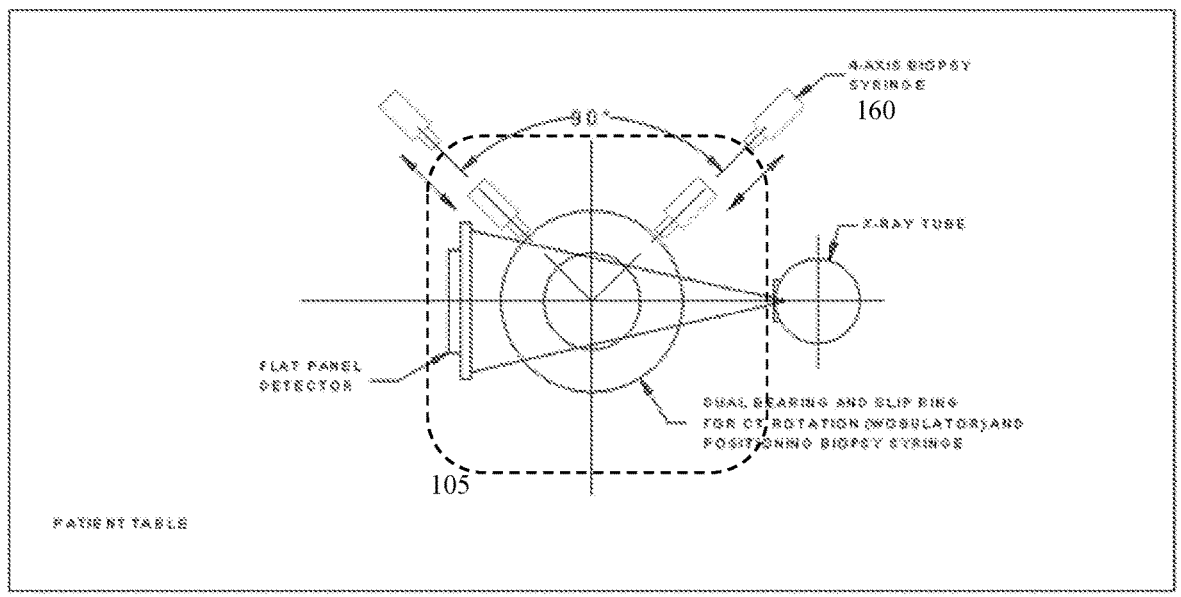
FIG. 3 depicts an example biopsy attachment for use with the system of FIG. 1, according to embodiments of the present disclosure.

In example embodiments such as depicted in FIG. 3, the improved CT imaging systems may further include a biopsy feature. Thus, for example, in some embodiments, a gantry 105 holding the x-ray generation 110 and the x-ray detection 120 assemblies can be configured to translate the x-ray generation 110 and x-ray detection assemblies, e.g., laterally, vertically, pivotally, etc., so as to allow for access for biopsy attachment 160 from multiple and opposite directions. In some embodiments, the biopsy feature 160 may include a biopsy device which may be controlled to provide access along a range of angles (e.g., 30-65 degrees) from either side. In further example embodiment, an integrated securing mechanism/feature may be included for securing the patient's anatomy for biopsy. In yet further embodiments, the improved CT imaging systems may further include a mechanism for automatically applying x-ray fiducial markers to the breast to facilitate surgical navigation, e.g., for a biopsy, based on acquired CT imaging data. In particular, the x-ray fiducial markers may be used to enable registration of surgical navigation imaging data with the acquired CT imaging data. In further example embodiments, the biopsy attachment 160 can be secured relative to the same gantry 105 holding the x-ray generation 110 and x-ray detection 120 assemblies. Thus, the biopsy attachment may be configured for automatic positioning based on the CT imaging data (which can be cross-registered to gantry position). Thus, the same gantry 105 for moving the x-ray generation 110 and x-ray detection 120 assemblies can be used to position the biopsy attachment.

With reference to FIG. 3, an example embodiment of a mechanism for producing the orbital and oscillating motions for the imaging system 100 in FIG. 1 is depicted. In particular a rotating slip ring 170 powered by an electric motor and timing belt drive 170 drive the orbital motion of gantry holding the x-ray generation and detection assemblies 110 and 120, while an oscillating actuator connecting the slip ring to the gantry drives the oscillation motion.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A CT imaging system comprising opposing x-ray generation and x-ray detector assemblies and a motion mechanism configured for simultaneously rotationally orbiting the x-ray generation and x-ray detector assemblies around a patient's anatomy along a main axis of rotation of the imaging system while rotationally oscillating the x-ray generation and x-ray detector assemblies about a spinning oscillation axis which is perpendicular to both the main axis of rotation and to a transmission axis extending between the x-ray generation and detector assemblies wherein the main axis of rotation corresponds with a longitudinal axis of a cavity configured for receiving a portion of a patient's anatomy to be imaged and wherein the cavity is defined by a patient support structure having graduated or angled support walls leading to the cavity and wherein the support walls define undulations corresponding with the oscillating motion of the x-ray generation assembly and the x-ray detection assembly.

2. The system of claim 1, wherein the orbiting and the oscillating motions are independent.

3. The system of claim 1, wherein the orbiting and the oscillating motions are dependent.

4. The system of claim 3, wherein an orbital position is determinative of a corresponding oscillation position.

5. The system of claim 3, wherein the motion mechanism is configured to result in a fixed number of oscillations per orbital rotation.

6. The system of claim 5, wherein the motion mechanism is configured to result in two or more oscillations per rotation.

7. The system of claim 3, wherein the motion mechanism uses a rotating slip ring and oscillating actuator.

8. The system of claim 1, wherein the x-ray detector assembly includes a high resolution flat-panel x-ray detector.

9. The system of claim 1, wherein the graduated or angled support walls define a conical or funnel type configuration.

10. The system of claim 1 wherein an angle of the support walls is configured to correspond with a position or orientation of the x-ray generation assembly or the x-ray detection assembly during peak oscillation.

11. The system of claim 1, wherein the undulations drive the oscillating motion of the x-ray generation assembly and the x-ray detection assembly.

12. The system of claim 1, wherein the patient support structure is constructed of a radiolucent material.

13. The system of claim 1, wherein the cavity further includes a changeable lining for enabling quick cleaning and sterilization of the cavity.

14. The system of claim 1, wherein the semi-flexible or elastic support sheath or netting is configured to stretch and mold to a shape of the patient's anatomy while still providing for support.

15. The system of claim 1 wherein the patient support structure further includes an interchangeable negative mold corresponding to a shape of the patient's anatomy fitted into the cavity and enabling the patient's anatomy to be held in a volumetrically secured position.

16. The system of claim 1 wherein the patient support structure further includes motorized means for positioning the patient into the supine position.

17. The system of claim 1, further including an integrated biopsy feature including a biopsy attachment.

18. The system of claim 1, wherein a gantry holding the x-ray generation and x-ray detection assemblies is configured to enable moving the x-ray generation and x-ray detection assemblies one or more of laterally, vertically or pivotally so as to allow for access for the biopsy attachment from multiple and opposite directions.

19. A CT imaging system comprising opposing x-ray generation and x-ray detector assemblies and a motion mechanism configured for simultaneously rotationally orbiting the x-ray generation and x-ray detector assemblies around a patient's anatomy along a main axis of rotation of the imaging system while rotationally oscillating the x-ray generation and x-ray detector assemblies about a spinning oscillation axis which is perpendicular to both the main axis of rotation and to a transmission axis extending between the x-ray generation and detector assemblies wherein the main axis of rotation corresponds with a longitudinal axis of a cavity configured for receiving a portion of a patient's anatomy to be imaged and wherein the cavity is defined by a patient support structure and configured to function as a sealed volumetric cavity once a patient's anatomy is received therein.

20. A CT imaging system comprising opposing x-ray generation and x-ray detector assemblies and a motion mechanism configured for simultaneously rotationally orbiting the x-ray generation and x-ray detector assemblies around a patient's anatomy along a main axis of rotation of the imaging system while rotationally oscillating the x-ray generation and x-ray detector assemblies about a spinning oscillation axis which is perpendicular to both the main axis of rotation and to a transmission axis extending between the x-ray generation and detector assemblies wherein the main axis of rotation corresponds with a longitudinal axis of a cavity configured for receiving a portion of a patient's anatomy to be imaged and wherein the cavity is defined by a patient support structure that includes a semi-flexible or elastic support sheath or netting over an opening to the cavity.

* * * * *

UNITED STATES PATENT AND TRADEMARK OFFICE
CERTIFICATE OF CORRECTION

PATENT NO. : 10,603,003 B2
APPLICATION NO. : 16/074102
DATED : March 31, 2020
INVENTOR(S) : Eric M. Bailey and Andrew Tybinkowski Page 1 of 1

It is certified that error appears in the above-identified patent and that said Letters Patent is hereby corrected as shown below:

On the Title Page

Item (73), The Assignee "Dedicating2Imaging, LLC." should read "Dedicated2Imaging, LLC."

Signed and Sealed this
Twenty-ninth Day of September, 2020

Andrei Iancu
*Director of the United States Patent and Trademark Office*